United States Patent
Terashima et al.

(10) Patent No.: US 6,767,450 B2
(45) Date of Patent: Jul. 27, 2004

(54) ION SELECTIVE ELECTRODE

(75) Inventors: Masaaki Terashima, Saitama (JP); Osamu Seshimoto, Saitama (JP); Yoshikazu Amano, Saitama (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/823,840

(22) Filed: Mar. 30, 2001

(65) Prior Publication Data
US 2001/0035356 A1 Nov. 1, 2001

(30) Foreign Application Priority Data
Mar. 30, 2000 (JP) ......................................... 2000-094333

(51) Int. Cl.[7] .......................................... G01N 27/333
(52) U.S. Cl. ........................ 205/792; 204/409; 204/416; 204/418
(58) Field of Search ............................. 204/416, 418, 204/409, 403, 433, 435, 403.01, 403.03; 205/787.5, 789, 789.5

(56) References Cited

U.S. PATENT DOCUMENTS

| | | | |
|---|---|---|---|
| 4,214,968 A | * | 7/1980 | Battaglia et al. ............. 204/418 |
| 4,437,970 A | * | 3/1984 | Kitajima et al. ............. 204/412 |
| H745 H | * | 2/1990 | Ishizuka et al. ............. 204/418 |
| 5,607,567 A | * | 3/1997 | Yun et al. ............... 204/403.08 |
| 5,911,862 A | * | 6/1999 | Chan ........................... 204/416 |

OTHER PUBLICATIONS

Terashima, Fujifilm Research & Development, vol. 46, pp. 56–62, 2001.*

* cited by examiner

Primary Examiner—Kaj K. Olsen
(74) Attorney, Agent, or Firm—Reed Smith LLP

(57) ABSTRACT

A composite ion selective electrode comprising a calcium ion selective electrode member and a hydrogen ion selective electrode member which is characterized in that a calcium ion selective membrane of the calcium ion selective electrode member has a thickness of 5 to 30 $\mu$m, and the hydrogen ion selective membrane of the hydrogen ion selective electrode member contains tri-n-dodecyl-amine and trisethylhexyl trimellitate. Each of the calcium ion selective electrode member and the hydrogen ion selective electrode member can be employed singly.

12 Claims, 4 Drawing Sheets

ION SELECTIVE ELECTRODE

This application claims priority of Japanese Application No. 2000-094333 filed Mar. 30, 2000, the complete disclosure of which is hereby incorporated by reference.

FIELD OF THE INVENTION

This invention relates to an ion selective electrode employable for determining a concentration of a calcium ion and/or a hydrogen ion in an aqueous sample. In particular, the invention relates to an ion selective electrode for potentiometrically determining a concentration of a calcium ion and/or a hydrogen ion existing in body fluids such as blood and serum.

BACKGROUND OF THE INVENTION

Various ions existing in body fluids, such as hydrogen ion, sodium ion, potassium ion, chloride ion, bromide ion, and iodide ion, can be quantitatively detected by means of an ion selective silver/silver halide electrode. Representative structure of the ion-selective electrode comprises, in order, an electro-insulating support, an electrode composite consisting essentially of a silver metal layer and a silver halide layer, an electrolyte layer, and an ion-selective membrane, the electrode composite being divided to give a pair of electrode units, and further comprising a reference liquid-receiving opening and a sample liquid-receiving opening each of which is provided on the ion-selective membrane of each electrode unit, and a bridge element having two terminals, one terminal being placed in the reference liquid-receiving opening and another terminal being placed in the sample liquid-receiving opening.

A composite ion selective electrode which comprises two or more ion selective electrode members in one structure is also known. The composite ion selective electrode is favorably employable for simultaneously determining concentrations of two or more different ions in a sample liquid.

Among the determination of concentration of various ions in a body fluid such as blood or serum, the determination of an ionic calcium is very important in the clinical test. The determination of an ionic calcium (i.e., calcium ion) in blood is necessary, for instance, when a patient is tested with respect to abnormal metabolism (for example, functional disorder of accessory thyroid or transfer of cancer to bone). Also important is the determination of concentration of hydrogen ion (in term of pH) in blood, because the pH value of the blood indicates an acid-base balance in the blood. Moreover, in most of the clinical tests, the ionic calcium concentration in blood is generally utilized after it is standardized in terms of a concentration value at pH 7.4. Therefore, it is of value that both of the calcium ion concentration and the hydrogen ion concentration are simultaneously determined in a simple procedure.

Since a clinical test device is frequently employed at home at the present time, it is advantageous that the ion selective electrode to be provided to the test device has a small size, as compared with the conventional ion selective electrode provided to the test device employed in hospitals or other medical treating facilities.

According to the study by the present inventors, most of the conventional ion selective electrodes, particularly, calcium ion selective electrodes and hydrogen ion selective electrodes give relatively poor analytical data. For instance, reproducibility of analytical data obtained in the use of different ion selective electrodes which have been produced using the same materials to give equivalent electrodes is not high. It is also noted that a response period for obtaining a constant analytical data is prolonged.

SUMMARY OF THE INVENTION

Accordingly, it is an object of the invention to provide a calcium ion selective electrode which shows good analytical reproducibility and which gives a constant analytical data within a short period of time after placing a sample liquid on the electrode.

Further, it is an object of the invention to provide a hydrogen ion selective electrode which shows good analytical reproducibility and which gives a constant analytical data within a short period of time after placing a sample liquid on the electrode.

Furthermore, it is an object of the invention to provide a composite ion selective electrode containing both of a calcium ion selective electrode and a hydrogen ion selective electrode, both of which show good analytical reproducibility and both of which give a constant analytical data within a short period of time after placing a sample liquid on the electrode. As a result of study of the present inventors, it has been discovered that the calcium ion selective electrode having a calcium ion selective membrane of a very small thickness gives good analytical results in the reproducibility of the analytical data and the response time. Further, it has been discovered the calcium ion selective membrane having a small thickness preferably contains calcium di[4-(1,1,3,3-tetramethylbutyl)phenyl] phosphate (t-HDOPP), particularly in combination with a vinyl acetate copolymer and dioctylphenyl phosphonate so as to obtain the analytical data of increased accuracy.

It is also discovered that the hydrogen ion selective electrode having a hydrogen ion selective membrane containing a combination of tri-n-dodecylamine and trisethylhexyl trimellitate (Tris EHT) gives analytical data with increased reproducibility. The hydrogen ion selective membrane preferably comprises a combination of tri-n-dodecylamine, trisethylhexyl trimellitate, potassium tetrakis (p-chlorophenyl borate), and a vinyl chloride-vinyl acetate copolymer, so as to increase analytical reproducibility.

Accordingly, the present invention resides in a composite ion selective electrode comprising (1) a calcium ion selective electrode member and a hydrogen ion selective electrode member,
   in which the calcium ion selective electrode member comprises an electro-insulating support, a pair of electrode units each of which comprises a silver layer and a silver halide layer, and which are electrically separated from each other, an electrolyte layer, and a calcium ion selective membrane, and
   in which the hydrogen ion selective electrode member comprises an electro-insulating support, a pair of electrode units each of which comprises a silver layer and a silver halide layer, and which are electrically separated from each other, an electrolyte layer, and a hydrogen ion selective membrane;

(2) an electro-insulating member having two openings in which one opening is provided for introducing a sample liquid into the composite electrode and another opening is provided for introducing a reference liquid into the composite electrode;

(3) a pair of distributing members in which one member distributes the introduced sample liquid to the ion selective membrane of each ion selective electrode member at a site corresponding to one electrode unit and in which another member distributes the introduced reference liquid to the ion selective membrane of each ion selective electrode member at a site corresponding to another electrode unit; and (4) a bridge member which is provided on the electro-insulating member to bridge the two openings of the electro-insulating member so as to electrically connect the introduced sample liquid and the introduced reference liquid;

which is characterized in that the calcium ion selective membrane has a thickness of 5 to 30 $\mu$m, and the hydrogen ion selective membrane contains tri-n-dodecyl-amine and trisethylhexyl trimellitate.

The invention further resides in a calcium ion selective electrode comprising (1) a calcium ion selective electrode member which comprises an electro-insulating support, a pair of electrode units each of which comprises a silver layer and a silver halide layer, and which are electrically separated from each other, an electrolyte layer, and a calcium ion selective membrane;

(2) an electro-insulating member having two openings which is provided on the calcium ion selective electrode member and in which one opening is provided for introducing a sample liquid into the composite electrode and another opening is provided for introducing a reference liquid into the composite electrode; and (3) a bridge member which is provided on the electro-insulating member to bridge the two openings of the electro-insulating member so as to electrically connect the introduced sample liquid and the introduced reference liquid;

which is characterized in that the calcium ion selective membrane has a thickness of 5 to 30 $\mu$m.

The invention furthermore resides in a hydrogen ion selective electrode comprising (1) a hydrogen ion selective electrode member which comprises an electro-insulating support, a pair of electrode units each of which comprises a silver layer and a silver halide layer, and which are electrically separated from each other, an electrolyte layer, and a hydrogen ion selective membrane;

(2) an electro-insulating member having two openings which is provided on the hydrogen ion selective electrode member and in which one opening is provided for introducing a sample liquid into the composite electrode and another opening is provided for introducing a reference liquid into the composite electrode; and (3) a bridge member which is provided on the electro-insulating member to bridge the two openings of the electro-insulating member so as to electrically connect the introduced sample liquid and the introduced reference liquid;

which is characterized in that the hydrogen ion selective membrane contains tri-n-dodecylamine and trisethylhexyl trimellitate.

DETAILED DESCRIPTION OF THE INVENTION

Figure 1:
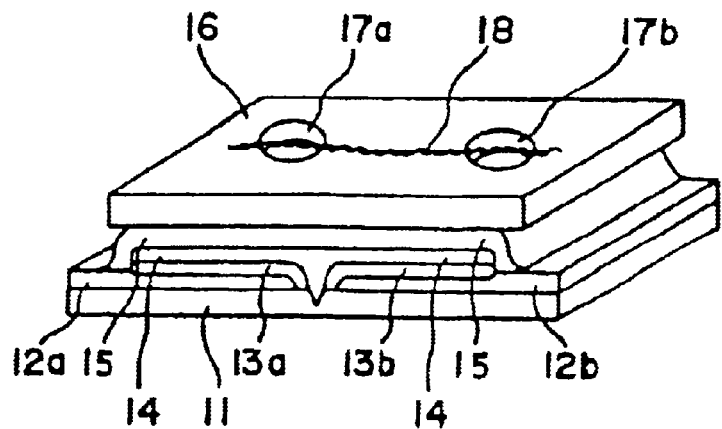
FIG. 1 schematically illustrates a structure of a representative ion selective electrode for determining a calcium ion or a hydrogen ion.

A representative structure of an ion selective silver/silver halide electrode is illustrated in FIG. 1.

The ion selective electrode of FIG. 1 is composed of:

(1) an ion selective electrode member which comprises an electro-insulating support 11, a pair of electrode units each of which comprises a silver layer 12a, 12b and a silver halide layer 13a, 13b, and which are electrically separated from each other, an electrolyte layer 14, and an ion selective membrane 15;

(2) an electro-insulating member 16 having two openings 17a, 17b which is provided on the ion selective electrode member and in which one opening 17a is provided for introducing a sample liquid into the composite electrode and another opening 17b is provided for introducing a reference liquid into the composite electrode; and (3) a bridge member 18 which is provided on the electro-insulating member 16 to bridge the two openings 17a, 17b of the electro-insulating member 16 so as to electrically connect the introduced sample liquid and the introduced reference liquid.

Figure 2:
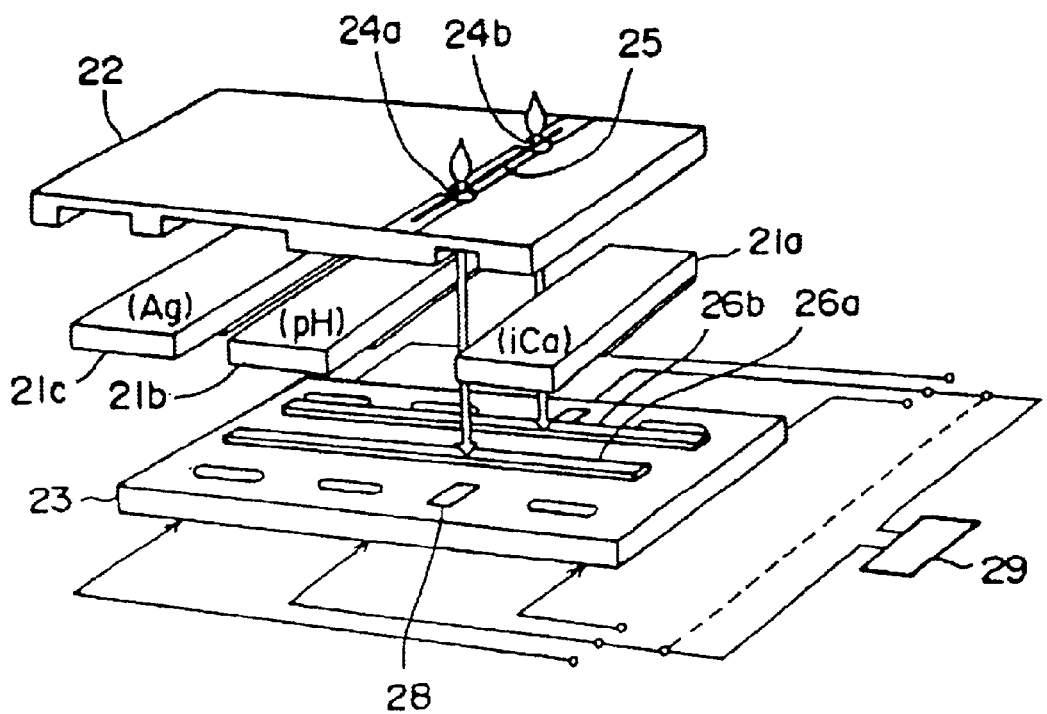
FIG. 2 schematically illustrates a structure of a representative composite ion selective electrode for determining both of calcium ion and hydrogen ion.

A representative structure of a composite ion selective electrode for analysis of concentration of calcium ion ($Ca^{2+}$ or iCa) and concentration of hydrogen ion ($H^+$ or pH) is illustrated in FIG. 2.

The composite ion selective electrode is composed of:

(1) a calcium ion selective electrode member 21a and a hydrogen ion selective electrode member 21b, both of which are placed in an electro-insulating lower frame 23, in which the calcium ion selective electrode member 21a comprises an electro-insulating support, a pair of electrode units each of which comprises a silver layer and a silver halide layer, and which are electrically separated from each other, an electrolyte layer, and a calcium ion selective membrane, and in which the hydrogen ion selective electrode member 21b comprises an electro-insulating support, a pair of electrode units each of which comprises a silver layer and a silver halide layer, and which are electrically separated from each other, an electrolyte layer, and a hydrogen ion selective membrane;

(2) an electro-insulating member (electro-insulating upper frame) 22 having two openings 24a, 24b in which one opening 24a is provided for introducing a sample liquid into the composite electrode and another opening 24b is provided for introducing a reference liquid into the composite electrode;

(3) a pair of distributing members 26a, 26b in which one member 26a distributes the introduced sample liquid to the ion selective membrane of each ion selective electrode member at a site corresponding to one electrode unit and in which another member 26b distributes the introduced reference liquid to the ion selective membrane of each ion selective electrode member at a site corresponding to another electrode unit; and (4) a bridge member 25 which is provided on the electro-insulating member to bridge the two openings of the electro-insulating member so as to electrically connect the introduced sample liquid and the introduced reference liquid.

In FIG. 2, 21c indicates a dummy electrode made of a silver metal plate or a silver metal-coated plate, which serves for facilitating electric discharge from the assembled composite ion selective electrode. An opening for inserting an electric terminal and a potentiometer for measuring the difference of electric potential between each of the electrode units are denoted by 28 and 29.

The composite ion selective electrode of the invention can be designed to have three or more ion selective electrode members for determining three or more ions in a sample liquid simultaneously.

The calcium ion selective membrane of the calcium ion selective electrode of the invention should have a thickness of 5 to 30 μm, preferably 5 to 20 μm, more preferably 10 to 18 μm. The calcium ion selective membrane of the calcium ion selective electrode of the invention preferably contains calcium di[4-(1, 1, 3, 3-tetramethylbutyl)phenyl] phosphate, and preferably comprises a vinyl chloride-vinyl acetate copolymer, dioctylphenyl phosphonate and calcium di[4-(1, 1, 3, 3-tetramethylbutyl)phenyl] phosphate. However other known components for the preparation of a calcium ion selective membrane can be employed.

The hydrogen ion selective membrane of the hydrogen ion selective electrode of the invention contains tri-n-dodecylamine (effective component) and trisethylhexyl trimellitate (plasticizer), and preferably comprises tri-n-dodecylamine, trisethylhexyl trimellitate, potassium tetrakis (p-chlorophenylborate) and a vinyl chloride-vinyl acetate copolymer. The hydrogen ion selective membrane preferably has a thickness of 5 to 30 μm.

The electrolyte layer preferably comprises sodium chloride.

The composite ion selective electrode, calcium ion selective electrode, and hydrogen ion selective electrode of the invention can be manufactured in the conventional manner using known materials, except for adjusting the thickness of the calcium ion selective membrane and preparing the hydrogen ion selective membrane using the specifically selected composition.

The conventional methods for manufacturing a variety of ion selective electrodes and materials employed for the manufacture are described, for instance, in Japanese Patent Publications No. 58-4981 and No. H4-50530; Japanese Patent Provisional Publications No. 52-142584, No. 57-17852, and No. 58-211648; U.S. Pat. No. 4,053,381, No. 4,171,246, and No. 4,214,968; and Research Disclosure No. 16113 (September, 1977).

The determination of standardized calcium ion in a sample blood can be made using the composite ion selective electrode of the invention in the method comprising the steps:

spotting a sample blood and a reference liquid onto openings of the electro-insulating member of the composite ion selective electrode, respectively;

measuring potentiometrically a calcium ion concentration and a hydrogen ion concentration in the sample blood; and incorporating the measured calcium ion concentration and the measured hydrogen ion concentration into the following equation to obtain a value of Log (standardized iCa):

$$\text{Log (standardized } iCa) = \text{Log } (iCa \text{ at } pH) - 0.22 \times (7.4 - pH)$$

in which iCa means a calcium ion concentration and pH means a hydrogen ion concentration.

Accordingly, the standardized calcium ion concentration (i.e., calcium ion concentration standardized at pH 7.4) in a sample blood can be obtained accurately by a simple sample spotting procedure using the composite ion selective electrode of the invention and the simple calculation.

The composite ion selective electrode, calcium ion selective electrode, and hydrogen ion selective electrode of the invention can be very favorably employed for the determination of the concentrations of calcium ion and hydrogen ion of 0.5 to 2.5 mM. However, they are also favorably employable for the determination of concentrations of calcium ion and hydrogen ion of a higher level and a lower level.

The present invention is further described by the following examples.

Example 1
Calcium Ion Selective Electrode

On a polyethylene terephthalate film (support, thickness: 188 μm, sizes: 30 mm×100 mm) was vacuum deposited a metal silver layer (thickness: approx. 800 nm). Both edges of the silver metal deposited layer was covered with a liquid polymer resist, and the center portion of the silver metal deposited layer was removed using a cutter to provide an insulating space.

The silver metal layer in the exposed area was brought into contact with an aqueous solution containing hydrochloric acid and a potassium hydrogen carbonate (36 mM/L of hydrochloric acid and 16 mM/L of potassium hydrogen carbonate) for approximately 60 seconds for catalytic oxidation-chlorination. Subsequently, the silver metal layer was washed with water and dried, to give a silver/silver chloride-coated electrode.

In purified water (240 g) were dissolved 28.8 g of sodium chloride and 192 g of ethanol, to prepare an electrolyte solution. The electrolyte solution was coated on the silver/silver chloride layer and dried under atmospheric conditions. The dried electrolyte layer had an amount of 2.1 g/m$^2$.

On the electrolyte layer was formed a calcium ion selective layer of 26 μm thick using the following composition. Composition of calcium ion selective layer Calcium di[4-(1,1,3,3-tetramethylbutyl)phenyl]

| Composition of calcium ion selective layer | |
|---|---|
| Calcium di[4-(1,1,3,3-tetramethylbutyl)phenyl] phosphate (t-HDOPP) | 0.3 g |
| Dioctylphenyl phosphonate (DOPP) | 3.0 g |
| Vinyl chloride-vinyl acetate copolymer (VYNS) | 3.0 g |
| Methyl ethyl ketone | 20 g |

The prepared calcium ion selective electrode was aged at 35° C. for 24 hours.

Using the aged calcium ion selective electrode, a calcium ion assembly illustrated in FIG. 1 was manufactured.

Example 2
Calcium Ion Selective Electrode

The procedures of Example 1 were repeated except for changing the thickness of the ion selective membrane to 15 μm.

Comparison Example 1

Calcium Ion Selective Electrode

The procedures of Example 1 were repeated except for changing the thickness of the ion selective membrane to 34 μm.

Evaluation of Calcium Ion Selective Electrode

The calcium ion selective electrode was evaluated using the sample liquid and reference liquid set forth in Table 1.

The evaluation procedure was performed by spotting the sample liquid and reference liquid on the openings of the ion selective assembly and measuring a standard deviation of the electric potential at 60 seconds after the spotting, by means of a potentiometer (FDC 800, available from Fuji Photo Film Co., Ltd.).

Figure 3:
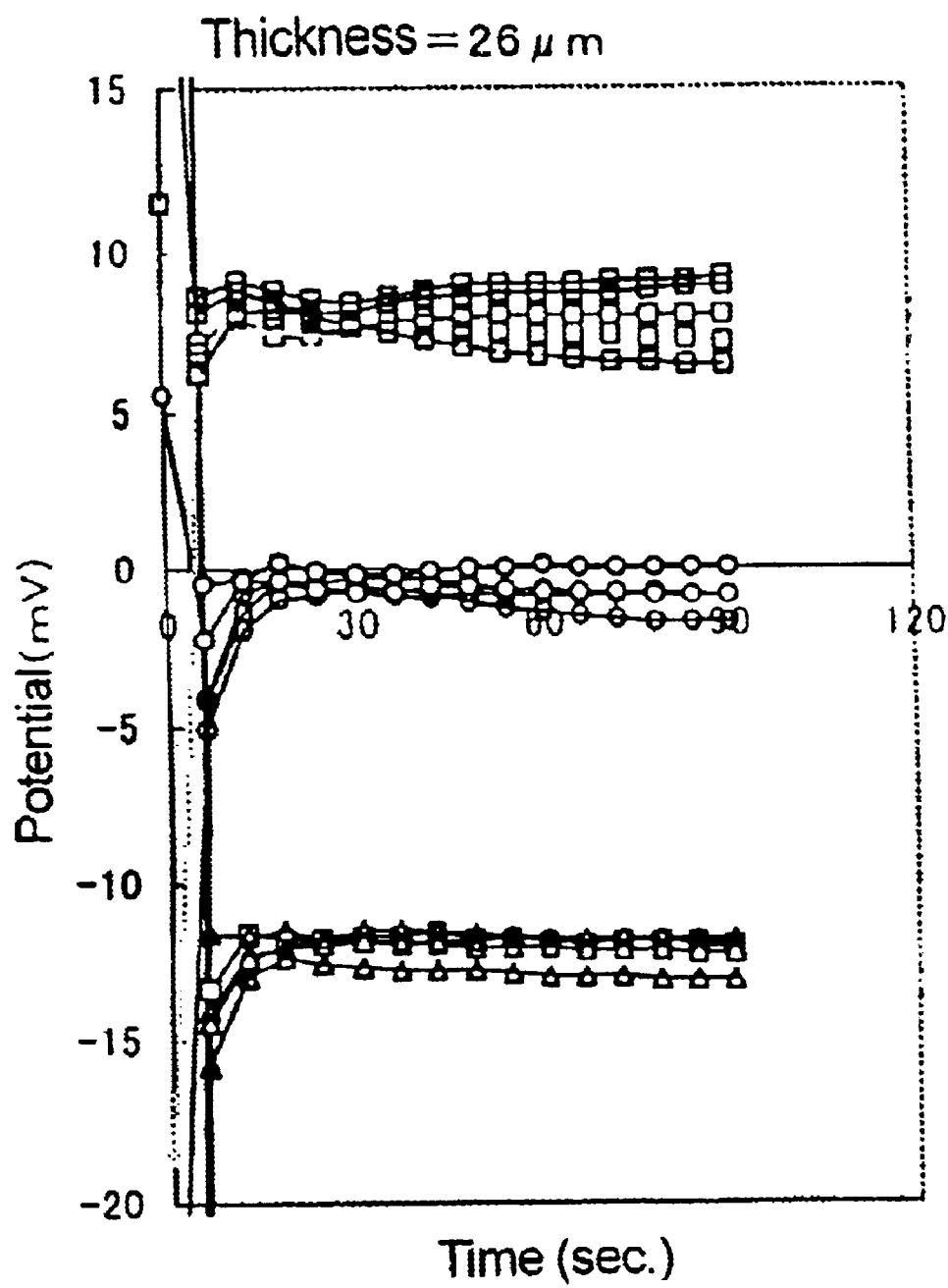
FIG. 3 is a graph indicating a relationship between a period of time and an electric potential observed in the use of an ion selective electrode of Example 1.
Figure 4:
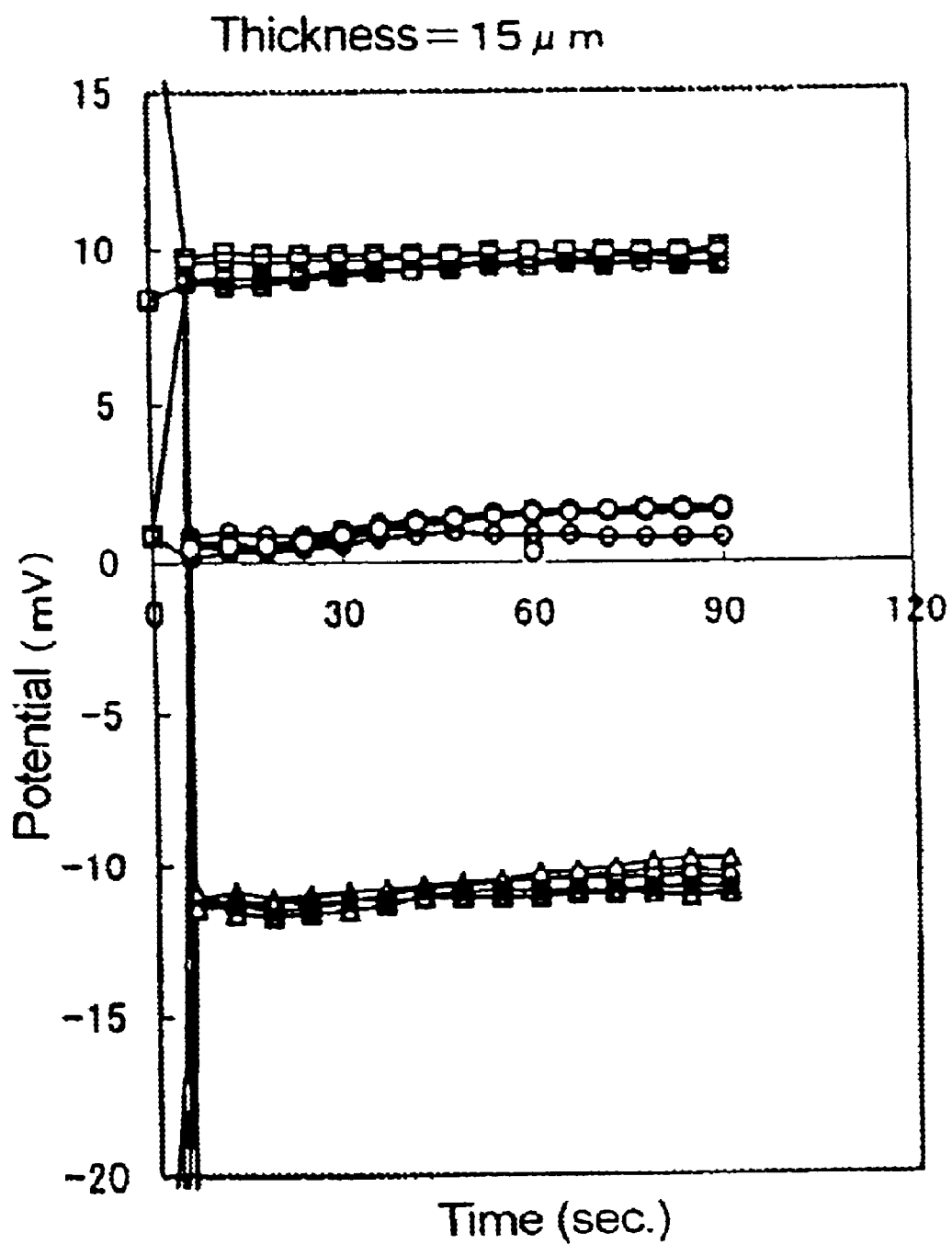
FIG. 4 is a graph indicating a relationship between a period of time and a electric potential observed in the use of an ion selective electrode of Example 2.
Figure 5:
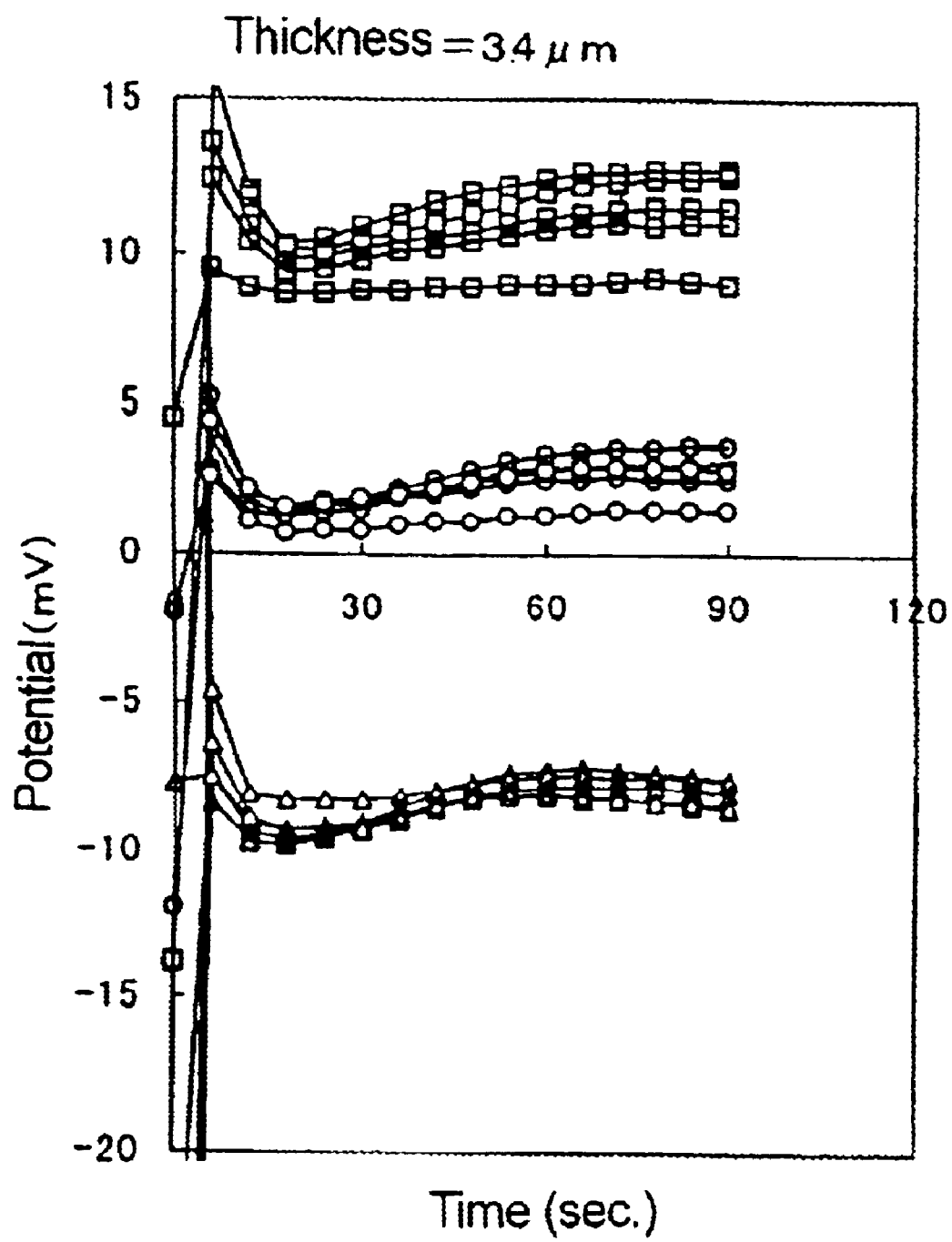
FIG. 5 is a graph indicating a relationship between a period of time and a electric potential observed in the use of an ion selective electrode of Comparison Example 1.

The results are set forth in Table 2 and FIGS. 3 to 5.

TABLE 1

|  | Sample Liquid | | | Reference |
| --- | --- | --- | --- | --- |
|  | L | M | H | Liquid |
| MOPS | 40 mM | 40 mM | 40 mM | 40 mM |
| NaCl | 160 mM | 160 mM | 160 mM | 160 mM |
| PVP K-15 | 3% | 3% | 3% | 3% |
| Glycerol | 2% | 2% | 2% | 2% |
| $CaCl_2$ | 0.5 mM | 1.25 mM | 2.5 mM | 1.25 mM |
| pH | 7.8 | 7.4 | 7.0 | 7.4 |

Remarks:
MOPS: 3-morpholinopropanesulfonic acid
PVP K-15: Polyvinylpyrrolidone K-15

Each of FIGS. 3, 4 and 5 graphically indicates a relationship between a period of time and an electric potential observed in the calcium ion selective electrodes of Example 1, Example 2 and Comparison Example 1, respectively.

TABLE 2

|  | Thickness of ion | SD (mV) | | |
| --- | --- | --- | --- | --- |
|  | selective membrane | L | M | H |
| Example 1 | 26 (μm) | 0.5 | 0.5 | 0.9 |
| Example 2 | 15 (μm) | 0.3 | 0.3 | 0.3 |
| Com. Ex. 1 | 34 (μm) | 0.4 | 0.8 | 1.3 |

As is apparent from the data set forth in Table 2 and FIGS. 3 to 5, the calcium ion selective electrodes of according to the invention (Examples 1 and 2) give a small standard deviation which means that the variation of analytical results is small.

Example 3

Hydrogen Ion Selective Electrode

On a polyethylene terephthalate film (support, thickness: 188 μm, sizes: 30 mm×100 mm) was vacuum deposited a metal silver layer (thickness: approx. 800 nm). Both edges of the silver metal deposited layer was covered with a liquid polymer resist, and the center portion of the silver metal deposited layer was removed using a cutter to provide an insulating space.

The silver metal layer in the exposed area was brought into contact with an aqueous solution containing hydrochloric acid and a potassium hydrogen carbonate (36 mM/L of hydrochloric acid and 16 mM/L of potassium hydrogen carbonate) for approximately 60 seconds for catalytic oxidation-chlorination. Subsequently, the silver metal layer was washed with water and dried, to give a silver/silver chloride-coated electrode.

In purified water (240 g) were dissolved 28.8 g of sodium chloride and 192 g of ethanol, to prepare an electrolyte solution. The electrolyte solution was coated on the silver/silver chloride layer and dried under atmospheric conditions. The dried electrolyte layer had an amount of 2.1 g/m².

On the electrolyte layer was formed a hydrogen ion selective layer of 20 μm thick using the following composition.

| Composition of hydrogen ion selective layer | |
| --- | --- |
| Tri-n-dodecylamine (TDDA) | 0.1 g |
| Trisethylhexyl trimellitate (Tris EHT) | 3.0 g |
| Potassium tetrakis (p-chlorophenyl borate) (KTpCPB) | 0.06 g |
| Vinyl chloride-vinyl acetate copolymer (VYNS) | 3.0 g |
| Methyl ethyl ketone | 20 g |

The prepared calcium ion selective electrode was aged at 35° C. for 24 hours.

Using the aged hydrogen ion selective electrode, a calcium ion assembly illustrated in FIG. 1 was manufactured.

Comparison Example 2

Hydrogen Ion Selective Electrode

The procedures of Example 3 were repeated except for replacing Tris MU (plasticizer of the hydrogen ion selective membrane) with dioctyl sebacate (DOS).

Comparison Example 3

Hydrogen Ion Selective Electrode

The procedures of Example 3 were repeated except for replacing Tris EHT (plasticizer of the hydrogen ion selective membrane) with dibutyl sebacate (DBS).

Comparison Example 4

Hydrogen Ion Selective Electrode

The procedures of Example 3 were repeated except for replacing Tris EHT (plasticizer of the hydrogen ion selective membrane) with nitrophenyl octyl ether (NPOE).

Evaluation of Hydrogen Ion Selective Electrode

The hydrogen ion selective electrode was stored at 45° C. for 3 weeks and then evaluated using the sample liquid and reference liquid set forth in Table 1.

The evaluation procedure was performed by spotting the sample liquid and reference liquid on the openings of the ion selective assembly and measuring a standard deviation of the electric potential at 60 seconds after the spotting, by means of a potentiometer (FDC 800, available from Fuji Photo Film Co., Ltd.). The measurement was repeated ten times.

The results are set forth in Tables 3 and 4.

TABLE 3

|  |  | SD (mV) | | |
| --- | --- | --- | --- | --- |
|  | Plasticizer | L | M | H |
| Example 3 | TrisEHT | 1.45 | 1.48 | 4.46 |
| Com. Ex. 2 | DOS | 4.47 | 5.35 | 4.46 |
| Com. Ex. 3 | DBS | 6.56 | 8.15 | 8.26 |
| Com. Ex. 4 | NPOE | 12.13 | 6.52 | 10.32 |

TABLE 4

| | Plasticizer | Average of Potential (mV) | | |
| | | L | M | H |
|---|---|---|---|---|
| Example 3 | TrisEHT | −21.70 | −1.86 | 21.99 |
| Com. Ex. 2 | DOS | −7.80 | 9.68 | 30.15 |
| Com. Ex. 3 | DBS | −1.59 | 3.86 | 4.77 |
| Com. Ex. 4 | NPOE | −9.92 | 6.72 | 28.25 |

As is apparent from the data set forth in Tables 3 and 4, the hydrogen ion selective electrode of according to the invention (Example 3) gives a small standard deviation which means that the variation of analytical results is small.

The average of potential observed in the hydrogen ion selective electrode of Example 3 is near to 0 at the M concentration level, which is appropriate. The averages of potential observed at the L and H concentration levels are far from the average observed at the M concentration level. This means that the dynamic range of the hydrogen ion selective electrode is wide which is favorably employable for analysis of a hydrogen ion concentration in a wide concentration range.

Example 4
Composite Ion Selective Electrode

The calcium ion selective electrode prepared in Example 2 and the hydrogen ion selective electrode prepared in Example 3 were employed for the preparation of a composite ion selective electrode in the form illustrated in FIG. 2.

What is claimed is:

1. A composite ion selective electrode comprising a calcium ion selective electrode member and a hydrogen ion selective electrode member, in which the calcium ion selective electrode member comprises an electro-insulating support, a first pair of electrode units each which comprises a silver layer and a silver halide layer, the pair of electrodes being electrically separated from each other, an electrolyte layer, and a calcium ion selective membrane, and in which the hydrogen ion selective electrode member comprises an electro-insulating support, a second pair of electrode units each of which comprises a silver layer and a silver halide layer, and which are electrically separated from each other, an electrolyte layer, and a hydrogen ion selective membrane;

(2) an electro-insulating member having two openings in which one opening is provided for introducing a sample liquid into one electrode of the calcium ion selective electrode of the calcium ion selective electrode member and one electrode of the hydrogen ion selective electrode member and another opening is provided for introducing a reference liquid into the composite electrode;

(3) a pair of distributing members in which one distributing member distributes the introduced sample liquid to the ion selective membrane of each ion selective electrode member at a site corresponding to one electrode unit and in which another distributing member distributes the introduced reference liquid to the ion selective membrane of each ion selective electrode member at a site corresponding to another electrode unit; and (4) a bridge member which is provided on the electro-insulating member to bridge the two openings of the electro-insulating member so as to electrically connect the introduced sample liquid and the introduced reference liquid;

which is characterized in that the calcium ion selective membrane has a thickness of 5 to 30 gym, and the hydrogen ion selective membrane contains tri-n-dodecylamine and trisethylhexyl trimellitate.

2. The composite ion selective electrode of claim 1, wherein the calcium ion selective membrane contains calcium di[4-(1,1,3,3-tetramethylbutyl)phenyl] phosphate.

3. The composite ion selective electrode of claim 1, wherein the calcium ion selective membrane comprises a vinyl chloride-vinyl acetate copolymer, dioctylphenyl phosphonate, and calcium di[4-(1,1,3,3-tetramethylbutyl) phenyl] phosphate.

4. The composite ion selective electrode of claim 1, wherein the thickness of calcium ion selective membrane is in the range of 5 to 20 μm.

5. The composite ion selective electrode of claim 4, wherein the thickness of calcium ion selective membrane is in the range of 10 to 18 μm.

6. The composite ion selective electrode of claim 1, wherein the hydrogen ion selective membrane has a thickness of 5 to 30 μm.

7. The composite ion selective electrode of claim 1, wherein the electrolyte layer comprises sodium chloride.

8. A method for determining a standardized calcium ion concentration in a sample blood, which comprises the steps of:

spotting a sample blood and a reference liquid onto openings of the electro-insulating member of the composite ion selective electrode of claim 1, measuring potentiometrically a calcium ion concentration and a hydrogen ion concentration in the sample blood; and incorporating the measured calcium ion concentration and he measured hydrogen ion concentration into the following the equation to obtain a value of Log (standardized iCa):

$$\text{Log(standardized } iCa) = \text{Log}(iCa \text{ at pH}) - 0.22 \times (7.4 - \text{pH})$$

in which iCa is a calcium ion concentration and pH is a hydrogen ion concentration.

9. A hydrogen ion selective electrode comprising (1) a hydrogen ion selective electrode member which comprises an electro-insulating support, a pair of electrode units each of which comprises a silver layer and a silver halide layer, the pair of electrodes being electrically separated from each other, an electrolyte layer, and a hydrogen ion selective membrane;

(2) an electro-insulating member having two openings which is provided on the hydrogen ion selective electrode member and in which one opening is provided for introducing a sample liquid into the another electrode of the calcium ion selective electrode member and another electrode of the hydrogen ion selective electrode member and another opening is provided for introducing a reference liquid into the another electrode of the calcium ion selective electrode member and another electrode of the hydrogen ion selective electrode member; and (3) a bridge member which is provided on the electro-insulating member to bridge the two openings of the electro-insulating member so as to electrically connect the introduced sample liquid and the introduced reference liquid;

which is characterized in that the hydrogen ion selective membrane contains tri-n-dodecylamine and trisethylhexyl trimellitate.

10. The hydrogen ion selective electrode of claim 9, wherein the hydrogen ion selective membrane further contains potassium tetrakis (p-chlorophenylborate) and a vinyl chloride-vinyl acetate copolymer.

11. The hydrogen ion selective electrode of claim 9, wherein the hydrogen ion selective membrane has a thickness of 5 to 30 $\mu$m.

12. The hydrogen ion selective electrode of claim 9, wherein the electrolyte layer comprises sodium chloride.

* * * * *